(12) United States Patent
Eichmuller et al.

(10) Patent No.: US 7,314,922 B1
(45) Date of Patent: Jan. 1, 2008

(54) CTAGE GENE FAMILY

(75) Inventors: Stefan Eichmuller, Edingen-Neckarhausen (DE); Dirk Schadendorf, Mannheim (DE); Dirk Usener, Mainz (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 666 days.

(21) Appl. No.: 10/110,807

(22) PCT Filed: Oct. 13, 2000

(86) PCT No.: PCT/DE00/03628

§ 371 (c)(1),
(2), (4) Date: Sep. 6, 2002

(87) PCT Pub. No.: WO01/27255

PCT Pub. Date: Apr. 19, 2001

(30) Foreign Application Priority Data

Oct. 14, 1999 (DE) .................... 199 49 595

(51) Int. Cl.
C07H 21/04 (2006.01)
C12N 15/00 (2006.01)

(52) U.S. Cl. ............... 536/23.1; 435/69.1; 435/252.3; 435/320.1

(58) Field of Classification Search ............ 536/23.1
See application file for complete search history.

(56) References Cited

U.S. PATENT DOCUMENTS

| | | | |
|---|---|---|---|
| 5,804,381 A | 9/1998 | Chen et al. | |
| 5,830,702 A | 11/1998 | Portnoy et al. | |
| 6,617,156 B1 * | 9/2003 | Doucette-Stamm et al. | 435/320.1 |
| 6,812,339 B1 * | 11/2004 | Venter et al. | 536/24.31 |

FOREIGN PATENT DOCUMENTS

WO    WO 96/14087    5/1996

OTHER PUBLICATIONS

Khyse-Anderson, Jan. "Electroblotting of multiple gels: a simple apparatus without buffer tank for rapid transfer of proteins from polyacylamide to nitrocellulose," Journal of Biochemical and Biophysical Methods, vol. 10, (1984), pp. 203-209.
Saki, Randall et al. "Analysis of enzymatically amplified β-globin and HLA-DQα DNA with allele-specific oligonucleotide probes," Nature, vol. 324, Nov. 13, 1986, pp. 163-166.
Rosenberg, Alan et al. "Vectors for selective expression of cloned DNAs by T7 RNA polymerase," Gene, vol. 56, (1987), 125-135.
Mannino, Raphael et al. "Liposome Mediated Gene Transfer," Bio/Techniques, vol. 6, No. 7, (1988), pp. 682-689.
Wiedmann, Martin et al. "Ligase Chain Reaction (LCR)—Overview and Applications," PCR Methods and Applications, vol. 3, (1994), pp. 551-564.
Scanlon, Kevin et al. "Oligonucleotide-mediated modulation of mammalian gene expression," The FASEB Journal, vol. 9, pp. 1288-1296.
Lavallie, Edward et al. "A Thioredoxin Gene Fusion Expression System That Circumvents Inclusion Body Formation in *E. coli* Cytoplasm," Bio/Technology, vol. 11, (1993), pp. 187-193.
Holmgren, Arne. "Thioredoxin," Ann. Rev. Biochem., vol. 54, (1985), 237-271.
Bock et al. "Hepatitis B Virus Genome is Organized into Nucleosomes in the Nucleus of the Infected Cell," Virus Genes, vol. 8, (1994), pp. 215-229.
Thoma et al. "Unravelled Nucleosomes, Nucleosome Beads and Higher Order Structures of Chromatin: Influence of Non-histone Components and Histone H1," J. Mol. Biol., vol. 149 (1981), pp. 709-733.
Lee, Se-Jin, et al.; Proliferin Secreted by Cultured Cells Binds to Mannose 6-Phosphate Receptors; The Journal of Biological Chemistry; vol. 263, No. 7, Mar. 5, 1988, pp. 3521-3527.
Wong, Sui-Lam; Advances in the use of *Bacillus subtilis* for the expression and secretion of heterologous proteins; Current Opioin in Biotechnology 1995, 6:517-522.
Romanos, Mike; Advances in the use of *Pichia pastoris* for high-level gene expression; Current Opinion in Biotechnology 1995, 6:527-533.
Davies, Anthony H.; Advances in the use of recombinant baculoviruses for the expression of heterologous proteins; Current Opinion in Biotechnology 1995, 6:543-547.
Williams, Keith L.; Recombinant glycoprotein production in the slime mould Dietyostelium discoideum; Current Opinion in Biotechnology 1995, 6:538-542.
Cao, Y., et al; Bispecific Antibodies as Novel Bioconjugates; Bioconjugate Chemistry, vol. 9, No. 6, Nov./Dec. 1998, pp. 635-644.
Taylor, Graham R., et al.; The polymerase chain reaction: new variations on an old theme; Current Opinion in Biotechnology 1995, 6:24-29.
Heckel, Dirk, et al. 1997. cDNA cloning and chromosomal mapping of a predicted coiled-coil proline-rich protein immunogenic in meningioma patients, Human Molecular Genetics, vol. 6, No. 12: 2031-2041.
EMBL:HSU73682. Heckel D., Meese E.U. Submitted Oct. 8, 1996 to the EMBL/GenBank/DDBJ databases.
Department of Gynecology, University of Saarland, Homburg, Germany and Ludwig Institute for Cancer Research, New York Branch, NY, USA 1998. Letter to the Editor, Int. J. Cancer, 78: 387-389.

(Continued)

*Primary Examiner*—Shanon Foley
*Assistant Examiner*—Laura B Goddard
(74) *Attorney, Agent, or Firm*—Steven J. Hultquist; Intellectual Property/Technology Law

(57) ABSTRACT

The present invention relates to a novel gene family for "cutaneous T-cell lymphoma associated genes" (CTAGE). The present invention describes two members of said family, CTAGE-1 and CTAGE-2, the underlying genes thereof and the use thereof for diagnosis and treatment of tumoral diseases.

8 Claims, 7 Drawing Sheets

OTHER PUBLICATIONS

Sahin, Ugur, Türeci, Özlem and Pfreundschuh, Michael, 1997. Serological identification of human tumor antigens, Cancer, pp. 709-716.

Heckel, D., Comtesse, N., Brass, N., Blin, N., Zang, K.D., and Meese, E. 1998. Novel immunogenic antigen homologous to nyaluronidase in meningioma, Human Molecular Genetics, vol. 7: 1859-1872.

Glass, L. Frank, Keller, Karen L., Messina, Jane L., Dalton, John, Yag-Howard, Cynthia and Fenske, Neil A. 1998. Cutaneous T-cell Lymphoma Cancer Control, vol. 5, No. 1: 11-18.

Jäger, Elke, Stockert, Elisabeth, Zidianakis, Zacharias, Chen, Yao-Tseng, Karbach, Julia, Jäger, Dirk, et al. 1999. Humoral Immune Responses of Cancer Patients Against "Cancer-Testis" Antigen Ny-Eso-I: Correlation With Clinical Events, Int. J. Cancer (Pred. Oncol.), 84: 506-510.

Zendman, Albert J.W., Cornelissen, Ine M.H.A., Weidle, Ulrich H., Ruiter, Dirk J., and van Muijen, Goos N.P. 1999. CTp11, a Novel Member of the Family of Human Cancer/Testis Antigens, Cancer Research 59: 6223-6229.

Eichmüller, Stefan, Usener, Dirk, Dummer, Reinhard, Stein, Angelika, Thiel, Daniela, and Schadendorf, Dirk 2001. Serological detection of cutaneous T-cell lymphoma-associated antigens, PNAS, vol. 98, No. 2: 629-634.

Ying, Han, et al. "Cancer therapy using a self-replicating RNA vaccine." Nature Medicine, vol. 5, (1999), pp. 823-827.

Nestle, Frank O., et al. "Vaccination of melanoma patients with peptide- or tumor lysate-pulsed dendritic cells." Nature Medicine, vol. 4, (1998), pp. 328-332.

Clay, Timothy M., et al. "Changes in the Fine Specificity of gp100$_{(209-217)}$-Reactive T Cells in Patients Following Vaccination with a Peptide Modified at an HLA-A2.1 Anchor Residue." Journal of Immunology, vol. 162, (1999), pp. 1749-1755.

Guzman, Carlos A., et al. "Attenuated *Listeria monocytogenes* carrier strains can deliver an HIV-1 gp120 T helper epitope to MHC class II-restricted human CD4 T cells." European Journal of Immunology, vol. 28, (1998), pp. 1807-1814.

Restifo, Nicholas, P. "The new vaccines: building viruses that elicit antitumor immunity." Immunology, vol. 8, (1996), pp. 658-663.

Medina, Eva, et al. "*Salmonella* vaccine carrier strains; effective delivery system to trigger anti-tumor immunity by oral route." European Journal of Immunology, vol. 29, (1999), pp. 693-699.

Conry, Robert M., et al. "Polynucleotide Immunization of Nonhuman Primates against Carcinoembryonic Antigen." Clinical Cancer Research, vol. 4, (1998) pp. 2903-2912.

Fynan, Ellen F., et al. "DNA vaccines: Protective immunizations by parental, mucosal, and gene-gun inoculations." Proc. Natl. Acad. Sci., vol. 90, (1993), pp. 11478-11482.

Nabel, Gary J. "Immune response in human melanoma after transfer of an allogeneic class 1 major histocompatibility complex gene with DNA-liposome complexes." Proc. Natl. Acad. Sci., vol. 93, (1996), pp. 15388-15393.

Kim, Christina, J. "Dendritic Cells Infected with Poxviruses Encoding MART-1/Melan A Sensitive T Lymphocytes In Vitro." Journal of Immunotherapy, vol. 20, (1997), pp. 276-286.

Weiskirch, Larry M., et al. "*Listeria monocytogenes*: a potent vaccine vector for neoplastic and infectious disease." Immunological Reviews, vol. 158, (1997), pp. 159-169.

Khyse-Anderson, Jan. "Electroblotting of multiple gels: a simple appartus without buffer tank for rapid transfer of proteins from polyacrylamide to nitrocellulose," Journal of Biochemical and Biophysical Methods, vol. 10, (1984), pp. 203-209.

Saki, Randall et al. "Analysis of enzymatically amplified β-globin and HLA-DQα DNA with allele-specific oligonucleotide probes," Nature, vol. 324, Nov. 13, 1986, pp. 163-166.

Rosenberg, Alan et al. "Vectors for selective expression of cloned DNAs by T7 RNA polymerase," Gene, vol. 56, (1987), 125-135.

Mannino, Raphael et al. "Liposome Mediated Gene Transfer," Bio/Techniques, vol. 6, No. 7, (1988), pp. 682-689.

Wiedmann, Martin et al. "Ligase Chain Reaction (LCR)—Overview and Applications," PCR Methods and Applications, vol. 3, (1994), pp. 551-564.

Scanlon, Kevin et al. "Oligonucleotide-mediated modulation of mammalian gene expression," The FASEB Journal, vol. 9, pp. 1288-1296, (1995).

Lavallie, Edward et al. "A Thioredoxin Gene Fusion Expression System That Circumvents Inclusion Body Formation in *E. coli* Cytoplasm," Bio/Technology, vol. 11, (1993), pp. 187-193.

Holmgren, Arne. "Thioredoxin," Ann. Rev. Biochem., vol. 54, (1985), 237-271.

Bock et al. "Hepatitis B Virus Genome is Organized into Nucleosomes in the Nucleus of the Infected Cell," Virus Genes, vol. 8, (1994), pp. 215-229.

Thoma et al. "Unravelled Nucleosomes, Nucleosome Beads and Higher Order Structures of Chromatin: Influence of Non-histone Components and Histone H1," J. Mol. Biol., vol. 149 (1981), pp. 709-733.

* cited by examiner

Sequence of CTAGE-1

```
     CTAATTTCTTCCTATGTTTGTCATCATATCATTACATAATTGTGTTGTTATTTCTTTTGT
1    ---------+---------+---------+---------+---------+---------+    60
     GATTAAAGAAGGATACAAACAGTAGTATAGTAATGTATTAACACAACAATAAAGAAAACA

TTTATTTTTATTTGGTGGGAACAACTTTATCCAGAACTTTTACTTGCCCCAGAATTATAT
61   ---------+---------+---------+---------+---------+---------+    120
     AAATAAAAATAAACCACCCTTGTTGAAATAGGTCTTGAAAATGAACGGGGTCTTAATATA

AGATCAGTTTCTCCTGACTTCTTTCCCAACCTTTACCTCTGTTGGTGTTCTAATAGTTTT
121  ---------+---------+---------+---------+---------+---------+    180
     TCTAGTCAAAGAGGACTGAAGAAAGGGTTGGAAATGGAGACAACCACAAGATTATCAAAA

AGTTTTATGTTCTGCTTTTCTCTTGCTGTGGCAAGGGGAAGGAGTAAATCTAAGATAGTG
181  ---------+---------+---------+---------+---------+---------+    240
     TCAAAATACAAGACGAAAAGAGAACGACACCGTTCCCCTTCCTCATTTAGATTCTATCAC

CTTAATTGCAGTTGGTGAATTTGATCTCTGATTGAGCTCTCTTCTCTGGAATTCTGTTAA
241  ---------+---------+---------+---------+---------+---------+    300
     GAATTAACGTCAACCACTTAAACTAGAGACTAACTCGAGAGAAGAGACCTTAAGACAATT

AAGATGAAATGTATCGTGTTCCCTGAGAGACGCCCTCAAATTTTGGATTAGTCCTTCATG
301  ---------+---------+---------+---------+---------+---------+    360
     TTCTACTTTACATAGCACAAGGGACTCTCTGCGGGAGTTTAAAACCTAATCAGGAAGTAC

CAAGCTGGGCCACCAAGCCATTGCTTCTTTTGGGGACAACCTGCCCTCACTTTTAAAAAG
361  ---------+---------+---------+---------+---------+---------+    420
     GTTCGACCCGGTGGTTCGGTAACGAAGAAAACCCCTGTTGGACGGGAGTGAAAATTTTTC

CATCCTAGCTCACATGCCTCCCCTAGCAGTTAATGCCACTCCAGTCTCTGCTTGAATGTA
421  ---------+---------+---------+---------+---------+---------+    480
     GTAGGATCGAGTGTACGGAGGGGATCGTCAATTACGGTGAGGTCAGAGACGAACTTACAT

ATAAAATAAAAGAAAAGTAACTATTTGAGACATGAGGTGCCCTTATTGTACACTGGGGCT
481  ---------+---------+---------+---------+---------+---------+    540
     TATTTTATTTTCTTTTCATTGATAAACTCTGTACTCCACGGGAATAACATGTGACCCCGA
```

Fig. 1

```
     TCCTATACATTTTCCGTCTTCCCTTGAACCACCACTATCCTCAGCTACTTTATGCTTCTG
541  ------+---------+---------+---------+---------+---------+  600
     AGGATATGTAAAAGGCAGAAGGGAACTTGGTGGTGATAGGAGTCGATGAAATACGAAGAC

TTCTGTTAAAGCCCTATTTGCTAGTGGAAAAATTTAACTCCTGGTGATTTTTTTAATACT
601  ---------+---------+---------+---------+---------+---------+  660
     AAGACAATTTCGGGATAAACGATCACCTTTTTAAATTGAGGACCACTAAAAAAATTATGA

AGGCCTCTTGCCTTCCTTCCAGTGAGAGAAAAATAGAATGGTAAGCCTAGTGGTTTCTTC
661  ---------+---------+---------+---------+---------+---------+  720
     TCCGGAGAACGGAAGGAAGGTCACTCTCTTTTTATCTTACCATTCGGATCACCAAAGAAG

CTTCACTGTTGAATACTATTTATCCAAGGTATCAAGGAAGAACTTCTAATCAGAAAAGAC
721  ---------+---------+---------+---------+---------+---------+  780
     GAAGTGACAACTTATGATAAATAGGTTCCATAGTTCCTTCTTGAAGATTAGTCTTTTCTG

ATGTATTATTTTCACAACTGGGTAGCATATCTCACTCCCAGAATGGAAGTTAGGTGGGAA
781  ---------+---------+---------+---------+---------+---------+  840
     TACATAATAAAAGTGTTGACCCATCGTATAGAGTGAGGGTCTTACCTTCAATCCACCCTT

TTGCAAGATTAAGGAGATTTTTCTGGATTTCTGTCTATGTATCATATCCACAGAACTCTT
841  ---------+---------+---------+---------+---------+---------+  900
     AACGTTCTAATTCCTCTAAAAAGACCTAAAGACAGATACATAGTATAGGTGTCTTGAGAA

TCTAGAGGAATTTTATATTGAGCCAGGCATCCATTTCCACAGTCTTGCATTTCTAGATAC
901  ---------+---------+---------+---------+---------+---------+  960
     AGATCTCCTTAAAATATAACTCGGTCCGTAGGTAAAGGTGTCAGAACGTAAAGATCTATG

TTCCAAAGTTATAGCACTGTTCCTAAATCATTTTTGGCTTTATTTATTAATTTATTGTTC
961  ---------+---------+---------+---------+---------+---------+  1020
     AAGGTTTCAATATCGTGACAAGGATTTAGTAAAAACCGAAATAAATAATTAAATAACAAG

ACTTCATTTCATTAGGTTCAGTATGAAACAGGTATTGTCATCTCTTTGTGTCTACTTTGC
1021 ---------+---------+---------+---------+---------+---------+  1080
     TGAAGTAAAGTAATCCAAGTCATACTTTGTCCATAACAGTAGAGAAACACAGATGAAACG
```

Fig. 1 (continuation)

```
        CACCTTTCCCCAGAATAGGCCTGAATGAGATTGAAAACGTTACTTCAGTTCCTTGTGTCT
1081    ---------+---------+---------+---------+---------+---------+    1140
        GTGGAAAGGGGTCTTATCCGGACTTACTCTAACTTTTGCAATGAAGTCAAGGAACACAGA

GACATTGCTTGTTTGTAACTAAGAAAAATAATATTTGCTTTTGTTGAATGACTACTAATT
1141    ---------+---------+---------+---------+---------+---------+    1200
        CTGTAACGAACAAACATTGATTCTTTTTATTATAAACGAAAACAACTTACTGATGATTAA

TTTTTCCATGAACCTAATAAACTAAAAAGAAAGTTGAAATAATAAAGAGTGAATAAGTAT
1201    ---------+---------+---------+---------+---------+---------+    1260
        AAAAAGGTACTTGGATTATTTGATTTTTCTTTCAACTTTATTATTTCTCACTTATTCATA

AAAAAAAAAAAAAAAAAAAAAAAAAAAAAA
1261    ---------+---------+---------+    1290
        TTTTTTTTTTTTTTTTTTTTTTTTTTTTTT
```

Fig. 1 (continuation)

CTAGE-2     4345 bp

```
   1 acgcggggag agcagccttg gcgctacgga ggagcctagg gctaaccctc agccatacct
  61 ggggctggtc ctggagttgc tacgcagggt tgtggcagca ctgactgaag gtatgagacc
 121 cgattctcat ccttatggtt ttccatggga attggtgata cgtgcagctg ttgctggatt
 181 ttttgctgtt ctcttcttgt ggagaagttt tagatcagtt acgagtcggc tttatgtgag
 241 aagagagaaa aagtttgctg tggcactttc tggactaatt gaagaaaaat gtaaactact
 301 tgaaaaattt agccttgttc aaaaagagta tgaaggctat gaagtagagt catcttttaaa
 361 gaatgccagc tttgagaagg aggcaacaga agcacaaagt ttggaggcaa cctgcgaaaa
 421 gctgaacagg ttcaattctg aacttgtgca tgaaatactc tgtctagaaa aagagttaaa
 481 agaagagaaa tctaaacatt ctgaacaaaa tgaattgatg gcggatattt ccaaaaggat
 541 acagtcgcta gaagatgagt caaatccct caatcacaa gtagctgaag ccaaaatgac
 601 cttcaagaga tttcaagcga atgaagaacg gttggagata gaaatacgag atgcttggaa
 661 agaaaattct gaacttcagg aaagccagaa acagcttttg caagaagctg aagtatggaa
 721 agaacaagtg agtgaactta ttaaacagaa aagaacattt gaagactcca agtacatgc
 781 agaacaagtt ctaaatgata aagaaaatca catcaagact ctgactgaac gcttgctaaa
 841 gatgaaagat ggggttgcta tgcttgaaga agatgtaacg gatgatgata acttggaatt
 901 agaaatgaac agtgaatcgg aagatggtgc ttacttagat aatcctccaa aaggagcttt
 961 gaagaaactg attcatgctg ctaagttaaa tgcttcctta aaaaccttag aaggagaaag
1021 aaaccaaatt tatattcaat tatctggagt tgataaaaca aaggaagagc ttacagagca
1081 tattaaaaat cttcagactg aacaagcatc tttgcagtca gaaaacacac attttgaaag
1141 tgagaatcag aagcttcagc agaaacttaa agtaatgact gaattatatc aagaaaatga
1201 aatgaaactc tacaggaaat taatagtaga ggaaaaatgc cggttagaga aagaagagaa
1261 actttctaaa gtagacgaaa tgatcagcca tgccactgaa gagctggaga cctaccgaaa
1321 gcgagccaaa gatcttaaag aatttgagaa aactattcat ttttatcaaa agaagattat
1381 tctccatgag aaaaaagcac gtgataattg gtcggcagct tggactgctg aaagaaacct
1441 caatgattta aggaaagaaa atgctcacaa cagacaaaaa ttaactgaaa tagagtttaa
1501 aataaaactt ttagaaaaag atccttatgg acttgatgtt ccaaatacag catttggcag
1561 acagcattcc ccatatggtc cctcaccatt gggttggcct tcatctgaaa cgagagcttc
1621 tctctatcct ccaactttgt tggaaggtcc tctcagactc tcacctttgc ttccacgggg
1681 aggaggaaga ggctccagag gcccagggaa tcctccggac catcagatta ccaaagaaag
1741 aggagaatca agctgtgata ggttaactga tcctcacagg gctccttctg acgctgggcc
1801 cctggcacct ccgtgggaac aggactatag gatgatgttt cctccaccag gacaatcata
1861 tcctgattca gctctccctc cacaaaggca agacagattt tattctaatt gtgctagact
1921 ctctggacca gcagaactca gaagtttaa tatgccttct ttggataaaa tggatgggtc
1981 aatgccttca gaatggaat ccagtagaaa tgatgccaaa gataatcttg gtaatttaaa
2041 ggtgcctgat tcatctctcc ccgctgaaaa tgaagcaact ggccctggct ttgttcctcc
2101 acctcttgct ccaatcagag gtttattgtt tccggtagat acaagggggcc cgttcataag
2161 aagaggacct cctttccccc cacctcctcc aggaaccgtg tttggagctt ctccagatta
2221 ttttttctcca agggatgtcc caggtccacc acgtgctcca tttgcaatga gaaatgtcta
```

Fig. 2

```
2281 tttaccgaga ggttttcttc cttaccgtcc cccaagacct gcattttttcc cccagccccc
2341 acattctgaa ggtagaatga gtttccatca gggttgagcc cgacttcaaa tgagcctgct
2401 gctgaacatc cagaacgaca gcaagaaacc taacaacatg tttgccctct tcaaaagtaa
2461 ttttgactga tctcattttc agtttaagta actgctgtta cttaagtgat tacactttg
2521 ttcagattga aacttaatgg aactataatt cccaggatag tatttgtaa atgaggatga
2581 tttaaatatg aatcttatga gtaaattatt tcattttatt ttattctaga tagtataact
2641 tttaatttga ttaatccact attatataaa gaatggtggg agctttatat atgtaatctt
2701 gcaggtgggg aggctttaaa ttgtctttat gtcaagaact gtatttactg tggttgtaga
2761 caaatgtgaa agtaacttta tgcttaaata agttttagtt gattaaaaaa atttaaaaaa
2821 tttaaaaaaa gaaatatata aatatgcaca ggtgggaagg tagaatacta tgtaactgtt
2881 agaatatttc actttaaacc aagatgatct tggatctcct gtcttataga ttttatatcc
2941 tctttcagta ctttgagagt gtaaaacatt tatagcagaa agtattcgtg tttcctctgt
3001 tttcctcaag aatggtttct tcgccctccc tttccttccc ttcgtcttcc ctaagctaat
3061 ttcttcctat gtttgtcatc atatcattac ataattgtgt tgtaacatcg gttgttttat
3121 ttagatttgg tgggaacaac tttatccaga acttttactt gccccagaat tatatagatc
3181 agtttctcct gacttctttc ccaacctttta cctctgttgg tgttctaata gttttagttt
3241 tatgttctgc ttttctcttg ctgtggcaag gggaaggagt aaatctaaga tagtgcttaa
3301 ttgcagttgg tgaatttgat ctctgattga gctctcttct ctggaattct gttaaaagat
3361 gaaatgtatc gtgttccctg agagacgccc tcaaattttg gattagtcct tcatgcaagc
3421 tgggccacca agccattgct tcttttgggg acaacctgcc ctcacttttta aaaagcatcc
3481 tagctcacat gcctcccta gcagttaatg ccactccagt ctctgcttga atgtaataaa
3541 ataaaagaaa agtaactatt tgagacatga ggtgcccta ttgtacactg gggcttccta
3601 tacattttcc gtcttccctt gaaccaccac tatcctcagc tactttatgc ttctgttctg
3661 ttaaagccct atttgctagt ggaaaaattt aactcctggt gatttttta atactaggcc
3721 tcttgccttc cttccagtga gagaaaaata gaatggtaag cctagtggtt tcttccttca
3781 ctgttgaata ctatttatcc aaggtatcaa ggaagaactt ctaatcagaa aagacatgta
3841 ttattttcac aactgggtag catatctcac tcccagaatg gaagttaggt gggaattgca
3901 agattaagga gatttttctg gatttctgtc tatgtatcat atccacagaa ctctttctag
3961 aggaatttta tattgagcca ggcatccatt tccacagtct tgcatttcta gatacttcca
4021 aagttatagc actgttccta aatcattttt ggctttattt attaatttat tgttcacttc
4081 atttcattag gttcagtatg aaacaggtat tgtcatctct ttgtgtctac tttgccacct
4141 ttccccagaa taggcctgaa tgagattgaa aacgttactt cagttccttg tgtctgacat
4201 tgcttgtttg taactaagaa aaataatatt tgcttttgtt gaatgactac taattttttt
4261 ccatgaacct aataaactaa aaagaaagtt gaaataataa agagtgaata agtataaaaa
4321 aaaaaaaaaa aaaaaaaaaa aaaaa
```

Fig. 2 (continuation)

CTAGE-2 protein    754 aa

```
  1 mrpdshpygf pwelviraav agffavlflw rsfrsvtsrl yvrrekkfav alsglieekc
 61 kllekfslvq keyegyeves slknasfeke ateaqsleat ceklnrfnse lvheilclek
121 elkeekskhs eqnelmadis kriqsledes kslksqvaea kmtfkrfqan eerleieird
181 awkenselqe sqkqllqeae vwkeqvseli kqkrtfedsk vhaeqvlndk enhiktlter
241 llkmkdgvam leedvtdddn lelemnsese dgayldnppk galkklihaa klnaslktle
301 gernqiyiql sgvdktkeel tehiknlqte qaslqsenth fesenqklqq klkvmtelyq
361 enemklyrkl iveekcrlek eeklskvdem ishateelet yrkrakdlke fektihfyqk
421 kiilhekkar dnwsaawtae rnlndlrken abnrqkltei efkikllekd pygldvpnta
481 fgrqhspygp splgwpsset raslyppt1l egplrlspll prgggrgsrg pgmppdhqit
541 kergesscdr ltdphrapsd agplappweq dyrmmfpppg qsypdsalpp qrqdrfysnc
601 arlsgpaelr sfnmpsldkm dgsmpsemes srndakdnlg nlkvpdsslp aeneatgpgf
661 vppplapirg llfpvdtrgp firrgppfpp pppgtvfgas pdyfsprdvp gpprapfamr
721 nvylprgflp yrpprpaffp qpphsegrms fhqg
```

Fig. 3

SEQUENCE LISTING

<160> NUMBER OF SEQ ID NOS: 6

<210> SEQ ID NO 1
<211> LENGTH: 1290
<212> TYPE: DNA
<213> ORGANISM: Homo sapiens

<400> SEQUENCE: 1

```
ctaatttctt cctatgtttg tcatcatatc attacataat tgtgttgtaa catcggttgt      60
tttatttaga tttggtggga acaactttat ccagaacttt tacttgcccc agaattatat     120
agatcagttt ctcctgactt cttttcccaac ctttacctct gttggtgttc taatagtttt    180
agttttatgt tctgcttttc tcttgctgtg gcaaggggaa ggagtaaatc taagatagtg    240
cttaattgca gttggtgaat ttgatctctg attgagctct cttctctgga attctgttaa    300
aagatgaaat gtatcgtgtt ccctgagaga cgccctcaaa ttttggatta gtccttcatg   360
caagctgggc caccaagcca ttgcttcttt tggggacaac ctgccctcac ttttaaaaag   420
catcctagct cacatgcctc ccctagcagt taatgccact ccagtctctg cttgaatgta    480
ataaaataaa agaaaagtaa ctatttgaga catgaggtgc ccttattgta cactgggct    540 tcctatacat tttccgtctt cccttgaacc accactatcc tcagctactt tatgcttctg   600
ttctgttaaa gccctatttg ctagtggaaa aatttaactc ctggtgattt ttttaatact   660
aggcctcttg ccttccttcc agtgagagaa aaatagaatg gtaagcctag tggtttcttc   720
cttcactgtt gaatactatt tatccaaggt atcaaggaag aacttctaat cagaaaagac   780
atgtattatt ttcacaactg ggtagcatat ctcactccca gaatggaagt taggtgggaa   840
ttgcaagatt aaggagattt ttctggattt ctgtctatgt atcatatcca cagaactctt   900
tctagaggaa tttttatattg agccaggcat ccatttccac agtcttgcat ttctagatac   960
ttccaaagtt atagcactgt tcctaaatca tttttggctt tatttattaa tttattgttc  1020
```

-continued

| | |
|---|---:|
| acttcatttc attaggttca gtatgaaaca ggtattgtca tctctttgtg tctactttgc | 1080 |
| cacctttccc cagaataggc ctgaatgaga ttgaaaacgt tacttcagtt ccttgtgtct | 1140 |
| gacattgctt gtttgtaact aagaaaaata atatttgctt ttgttgaatg actactaatt | 1200 |
| tttttccatg aacctaataa actaaaaaga aagttgaaat aataaagagt gaataagtat | 1260 |
| aaaaaaaaaa aaaaaaaaaa aaaaaaaaa | 1290 |

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2

| | |
|---|---:|
| ctcctgactt ctttcccaac ctttacc | 27 |

<210> SEQ ID NO 3
<211> LENGTH: 27
<212> TYPE: DNA
<213> ORGANISM: Artificial
<220> FEATURE:
<223> OTHER INFORMATION: primer

<400> SEQUENCE: 3

| | |
|---|---:|
| tgcaattccc acctaacttc cattctg | 27 |

<210> SEQ ID NO 4
<211> LENGTH: 4345
<212> TYPE: DNA
<213> ORGANISM: Homo sapiens

<400> SEQUENCE: 4

| | |
|---|---:|
| acgcggggag agcagccttg gcgctacgga ggagcctagg gctaaccctc agccatacct | 60 |
| ggggctggtc ctggagttgc tacgcagggt tgtggcagca ctgactgaag gtatgagacc | 120 |
| cgattctcat ccttatggtt ttccatggga attggtgata cgtgcagctg ttgctggatt | 180 |
| ttttgctgtt ctcttcttgt ggagaagttt tagatcagtt acgagtcggc tttatgtgag | 240 |
| aagagagaaa aagtttgctg tggcactttc tggactaatt gaagaaaaat gtaaactact | 300 |
| tgaaaatttt agccttgttc aaaaagagta tgaaggctat gaagtagagt catctttaaa | 360 |
| gaatgccagc tttgagaagg aggcaacaga agcacaaagt ttggaggcaa cctgcgaaaa | 420 |
| gctgaacagg ttcaattctg aacttgtgca tgaaatactc tgtctagaaa aagagttaaa | 480 |
| agaagagaaa tctaaacatt ctgaacaaaa tgaattgatg gcggatattt ccaaaaggat | 540 |
| acagtcgcta gaagatgagt caaatccct caaatcacaa gtagctgaag ccaaaatgac | 600 |
| cttcaagaga tttcaagcga atgaagaacg gttggagata gaaatacgag atgcttggaa | 660 |
| agaaaattct gaacttcagg aaagccagaa acagcttttg caagaagctg aagtatggaa | 720 |
| agaacaagtg agtgaactta ttaaacagaa aagaacattt gaagactcca agtacatgc | 780 |
| agaacaagtt ctaaatgata agaaaaatca catcaagact ctgactgaac gcttgctaaa | 840 |
| gatgaaagat ggggttgcta tgcttgaaga agatgtaacg gatgatgata acttggaatt | 900 |
| agaaatgaac agtgaatcgg aagatggtgc ttacttagat aatcctccaa aaggagcttt | 960 |
| gaagaaactg attcatgctg ctaagttaaa tgcttcctta aaaaccttag aaggagaaag | 1020 |
| aaaccaaatt tatattcaat tatctggagt tgataaaaca aaggaagagc ttacagagca | 1080 |
| tattaaaaat cttcagactg aacaagcatc tttgcagtca gaaaacacac atttttgaaag | 1140 |

-continued

```
tgagaatcag aagcttcagc agaaacttaa agtaatgact gaattatatc aagaaaatga   1200
aatgaaactc tacaggaaat taatagtaga ggaaaaatgc cggttagaga agaagagaa    1260 actttctaaa gtagacgaaa tgatcagcca tgccactgaa gagctggaga cctaccgaaa   1320
gcgagccaaa gatcttaaag aatttgagaa aactattcat ttttatcaaa agaagattat   1380
tctccatgag aaaaagcac gtgataattg gtcggcagct tggactgctg aaagaaacct    1440
caatgattta aggaaagaaa atgctcacaa cagacaaaaa ttaactgaaa tagagtttaa   1500
aataaaactt ttagaaaaag atccttatgg acttgatgtt ccaaatacag catttggcag   1560
acagcattcc ccatatggtc cctcaccatt gggttggcct tcatctgaaa cgagagcttc   1620
tctctatcct ccaactttgt tggaaggtcc tctcagactc tcacctttgc ttccacgggg   1680
aggaggaaga ggctccagag gcccagggaa tcctccggac catcagatta ccaaagaaag   1740
aggagaatca agctgtgata ggttaactga tcctcacagg gctccttctg acgctgggcc   1800
cctggcacct ccgtgggaac aggactatag gatgatgttt cctccaccag acaatcata   1860 tcctgattca gctctccctc acaaaggca agacagattt tattctaatt gtgctagact    1920
ctctggacca gcagaactca gaagttttaa tatgccttct ttggataaaa tggatgggtc   1980
aatgccttca gaaatggaat ccagtagaaa tgatgccaaa gataatcttg gtaatttaaa   2040
ggtgcctgat tcatctctcc ccgctgaaaa tgaagcaact ggccctggct ttgttcctcc   2100
acctcttgct ccaatcagag gtttattgtt tccggtagat acaagggggc cgttcataag   2160
aagaggacct cctttccccc cacctcctcc aggaaccgtg tttggagctt ctccagatta   2220
tttttctcca agggatgtcc caggtccacc acgtgctcca tttgcaatga gaaatgtcta   2280
tttaccgaga ggttttcttc cttaccgtcc cccaagacct gcattttttcc cccagccccc   2340 acattctgaa ggtagaatga gtttccatca gggttgagcc cgacttcaaa tgagcctgct   2400
gctgaacatc cagaacgaca gcaagaaacc taacaacatg tttgccctct tcaaaagtaa   2460
ttttgactga tctcattttc agtttaagta actgctgtta cttaagtgat tacacttttg   2520
ttcagattga aacttaatgg aactataatt cccaggatag tattttgtaa atgaggatga   2580
tttaaatatg aatcttatga gtaaattatt tcattttatt ttattctaga tagtataact   2640
tttaatttga ttaatccact attatataaa gaatggtggg agctttatat atgtaatctt   2700
gcaggtgggg aggctttaaa ttgtctttat gtcaagaact gtatttactg tggttgtaga   2760
caaatgtgaa agtaacttta tgcttaaata agttttagtt gattaaaaaa atttaaaaaa   2820
tttaaaaaaa gaaatatata aatatgcaca ggtgggaagg tagaatacta tgtaactgtt   2880
agaatatttc actttaaacc aagatgatct tggatctcct gtcttataga ttttatatcc   2940
tctttcagta ctttgagagt gtaaaacatt tatagcagaa agtattcgtg tttcctctgt   3000
tttcctcaag aatggtttct tcgccctccc ttttccttccc ttcgtcttcc ctaagctaat   3060
ttcttcctat gtttgtcatc atatcattac ataattgtgt tgtaacatcg gttgtttat    3120 ttagatttgg tgggaacaac tttatccaga acttttactt gccccagaat tatatagatc   3180
agtttctcct gacttctttc ccaacctta cctctgttgg tgttctaata gttttagttt     3240
tatgttctgc ttttctcttg ctgtggcaag gggaaggagt aaatctaaga tagtgcttaa   3300
ttgcagttgg tgaatttgat ctctgattga gctctcttct ctggaattct gttaaaagat   3360
gaaatgtatc gtgttccctg agagacgccc tcaaatttg gattagtcct tcatgcaagc    3420
tgggccacca agccattgct tctttgggg acaacctgcc ctcactttta aaagcatcc     3480
```

-continued

```
tagctcacat gcctcccta gcagttaatg ccactccagt ctctgcttga atgtaataaa      3540 ataaagaaa agtaactatt tgagacatga ggtgccctta ttgtacactg gggcttccta      3600
tacattttcc gtcttccctt gaaccaccac tatcctcagc tactttatgc ttctgttctg      3660
ttaaagccct atttgctagt ggaaaaattt aactcctggt gattttttta atactaggcc      3720
tcttgccttc cttccagtga gagaaaaata gaatggtaag cctagtggtt tcttccttca      3780
ctgttgaata ctatttatcc aaggtatcaa ggaagaactt ctaatcagaa aagacatgta      3840
ttattttcac aactgggtag catatctcac tcccagaatg gaagttaggt gggaattgca      3900
agattaagga gattttctg gatttctgtc tatgtatcat atccacagaa ctctttctag      3960
aggaatttta tattgagcca ggcatccatt tccacagtct tgcatttcta gatacttcca      4020
aagttatagc actgttccta aatcattttt ggctttattt attaatttat tgttcacttc      4080
atttcattag gttcagtatg aaacaggtat tgtcatctct ttgtgtctac tttgccacct      4140
ttccccagaa taggcctgaa tgagattgaa aacgttactt cagttccttg tgtctgacat      4200
tgcttgtttg taactaagaa aaataatatt tgcttttgtt gaatgactac taattttttt      4260
ccatgaacct aataaactaa aaagaaagtt gaaataataa agagtgaata agtataaaaa      4320
aaaaaaaaaa aaaaaaaaaa aaaaa                                           4345
```

<210> SEQ ID NO 5
<211> LENGTH: 754
<212> TYPE: PRT
<213> ORGANISM: Homo sapiens

<400> SEQUENCE: 5

```
Met Arg Pro Asp Ser His Pro Tyr Gly Phe Pro Trp Glu Leu Val Ile
1               5                   10                  15

Arg Ala Ala Val Ala Gly Phe Phe Ala Val Leu Phe Leu Trp Arg Ser
                20                  25                  30

Phe Arg Ser Val Thr Ser Arg Leu Tyr Val Arg Arg Glu Lys Lys Phe
            35                  40                  45

Ala Val Ala Leu Ser Gly Leu Ile Glu Glu Lys Cys Lys Leu Leu Glu
        50                  55                  60

Lys Phe Ser Leu Val Gln Lys Glu Tyr Glu Gly Tyr Glu Val Glu Ser
65                  70                  75                  80

Ser Leu Lys Asn Ala Ser Phe Glu Lys Glu Ala Thr Glu Ala Gln Ser
                85                  90                  95

Leu Glu Ala Thr Cys Glu Lys Leu Asn Arg Phe Asn Ser Glu Leu Val
            100                 105                 110

His Glu Ile Leu Cys Leu Glu Lys Glu Leu Lys Glu Glu Lys Ser Lys
        115                 120                 125

His Ser Glu Gln Asn Glu Leu Met Ala Asp Ile Ser Lys Arg Ile Gln
    130                 135                 140

Ser Leu Glu Asp Glu Ser Lys Ser Leu Lys Ser Gln Val Ala Glu Ala
145                 150                 155                 160

Lys Met Thr Phe Lys Arg Phe Gln Ala Asn Glu Glu Arg Leu Glu Ile
                165                 170                 175

Glu Ile Arg Asp Ala Trp Lys Glu Asn Ser Glu Leu Gln Glu Ser Gln
            180                 185                 190

Lys Gln Leu Leu Gln Glu Ala Glu Val Trp Lys Glu Gln Val Ser Glu
        195                 200                 205

Leu Ile Lys Gln Lys Arg Thr Phe Glu Asp Ser Lys Val His Ala Glu
    210                 215                 220
```

```
Gln Val Leu Asn Asp Lys Glu Asn His Ile Lys Thr Leu Thr Glu Arg
225                 230                 235                 240

Leu Leu Lys Met Lys Asp Gly Val Ala Met Leu Glu Glu Asp Val Thr
            245                 250                 255

Asp Asp Asp Asn Leu Glu Leu Glu Met Asn Ser Glu Ser Glu Asp Gly
                260                 265                 270

Ala Trp Leu Asp Asn Pro Pro Lys Gly Ala Leu Lys Lys Leu Ile His
        275                 280                 285

Ala Ala Lys Leu Asn Ala Ser Leu Lys Thr Leu Glu Gly Glu Arg Asn
    290                 295                 300

Gln Ile Tyr Ile Gln Leu Ser Gly Val Asp Lys Thr Lys Glu Glu Leu
305                 310                 315                 320

Thr Glu His Ile Lys Asn Leu Gln Thr Glu Gln Ala Ser Leu Gln Ser
                325                 330                 335

Glu Asn Thr His Phe Glu Ser Glu Asn Gln Lys Leu Gln Gln Lys Leu
                340                 345                 350

Lys Val Met Thr Glu Leu Tyr Gln Glu Asn Glu Met Lys Leu Tyr Arg
            355                 360                 365

Lys Leu Ile Val Glu Glu Lys Cys Arg Leu Glu Lys Glu Glu Lys Leu
        370                 375                 380

Ser Lys Val Asp Glu Met Ile Ser His Ala Thr Glu Glu Leu Glu Thr
385                 390                 395                 400

Tyr Arg Lys Arg Ala Lys Asp Leu Lys Glu Phe Glu Lys Thr Ile His
                405                 410                 415

Phe Tyr Gln Lys Lys Ile Ile Leu His Glu Lys Lys Ala Arg Asp Asn
                420                 425                 430

Trp Ser Ala Ala Trp Thr Ala Glu Arg Asn Leu Asn Asp Leu Arg Lys
        435                 440                 445

Glu Asn Ala His Asn Arg Gln Lys Leu Thr Glu Ile Glu Phe Lys Ile
    450                 455                 460

Lys Leu Leu Glu Lys Asp Pro Tyr Gly Leu Ser Val Pro Asn Thr Ala
465                 470                 475                 480

Phe Gly Arg Gln His Ser Pro Tyr Gly Pro Ser Pro Leu Gly Trp Pro
                485                 490                 495

Ser Ser Glu Thr Arg Ala Ser Leu Tyr Pro Pro Thr Leu Leu Glu Gly
            500                 505                 510

Pro Leu Arg Leu Ser Pro Leu Leu Pro Arg Gly Gly Arg Gly Ser
        515                 520                 525

Arg Gly Pro Gly Asn Pro Pro Asp His Gln Ile Thr Lys Glu Arg Gly
    530                 535                 540

Glu Ser Ser Cys Asp Arg Leu Thr Asp Pro His Arg Ala Pro Ser Asp
545                 550                 555                 560

Ala Gly Pro Leu Ala Pro Pro Trp Glu Gln Asp Tyr Arg Met Met Phe
                565                 570                 575

Pro Pro Pro Gly Gln Ser Tyr Pro Asp Ser Ala Leu Pro Pro Gln Arg
            580                 585                 590

Gln Asp Arg Phe Tyr Ser Asn Cys Ala Arg Leu Ser Gly Pro Ala Glu
        595                 600                 605

Leu Arg Ser Phe Asn Met Pro Ser Leu Asp Lys Met Asp Gly Ser Met
    610                 615                 620

Pro Ser Glu Met Glu Ser Ser Arg Asn Asp Ala Lys Asp Asn Leu Gly
625                 630                 635                 640
```

```
Asn Leu Lys Val Pro Asp Ser Ser Leu Pro Ala Glu Asn Glu Ala Thr
            645                 650                 655
Gly Pro Gly Phe Val Pro Pro Leu Ala Pro Ile Arg Gly Leu Leu
            660                 665                 670
Phe Pro Val Asp Thr Arg Gly Pro Phe Ile Arg Arg Gly Pro Pro Phe
            675                 680                 685
Pro Pro Pro Pro Pro Gly Thr Val Phe Gly Ala Ser Pro Asp Tyr Phe
            690                 695                 700
Ser Pro Arg Asp Val Pro Gly Pro Pro Arg Ala Pro Phe Ala Met Arg
705                 710                 715                 720
Asn Val Tyr Leu Pro Arg Gly Phe Leu Pro Tyr Arg Pro Arg Pro
                725                 730                 735
Ala Phe Phe Pro Gln Pro Pro His Ser Glu Gly Arg Met Ser Phe His
            740                 745                 750
Gln Gly
```

<210> SEQ ID NO 6
<211> LENGTH: 1290
<212> TYPE: DNA
<213> ORGANISM: Homo sapiens

<400> SEQUENCE: 6

```
gattaaagaa ggatacaaac agtagtatag taatgtatta acacaacaat aaagaaaaca      60
aaataaaaat aaaccaccct tgttgaaata ggtcttgaaa atgaacgggg tcttaatata     120
tctagtcaaa gaggactgaa gaaaggttg gaaatggaga caaccacaag attatcaaaa     180
tcaaaataca agacgaaaag agaacgacac cgttcccctt cctcatttag attctatcac     240
gaattaacgt caaccactta aactagagac taactcgaga gaagagacct aagacaatt     300
ttctactta catagcacaa gggactctct gcgggagttt aaaacctaat caggaagtac     360
gttcgacccg gtggttcggt aacgaagaaa acccctgttg acgggagtg aaaatttttc     420
gtaggatcga gtgtacggag gggatcgtca attacggtga ggtcagagac gaacttacat     480
tatttttattt tcttttcatt gataaactct gtactccacg gaataacat gtgaccccga     540
aggatatgta aaaggcagaa gggaacttgg tggtgatagg agtcgatgaa atacgaagac     600
aagacaattt cgggataaac gatcaccttt ttaaattgag gaccactaaa aaattatga     660
tccggagaac ggaaggaagg tcactctctt tttatcttac cattcggatc accaaagaag     720
gaagtgacaa cttatgataa ataggttcca tagttccttc ttgaagatta gtcttttctg     780
tacataataa aagtgttgac ccatcgtata gagtgagggt cttaccttca atccacccct     840
aacgttctaa ttcctctaaa aagacctaaa gacagataca tagtataggt gtcttgagaa     900
agatctcctt aaaatataac tcggtccgta ggtaaaggtg tcagaacgta aagatctatg     960
aaggtttcaa tatcgtgaca aggatttagt aaaaaccgaa ataaataatt aaataacaag    1020
tgaagtaaag taatccaagt catactttgt ccataacagt agagaaacac agatgaaacg    1080
gtggaaaggg gtcttatccg gacttactct aactttttgca atgaagtcaa ggaacacaga    1140
ctgtaacgaa caaacattga ttcttttttat tataaacgaa acaacttac tgatgattaa    1200
aaaaaggtac ttggattatt tgattttct ttcaactttta ttatttctca cttattcata    1260
tttttttttt tttttttttt tttttttttt                                    1290
```

CTAGE GENE FAMILY

CROSS-REFERENCE TO RELATED APPLICATIONS

This application is filed under the provisions of 35 U.S.C. §371 and claims the priority of International Patent Application No. PCT/DE00/03628 filed Oct. 13, 2000, which in turn claims priority of German Patent Application No. 199 49 595.5 filed Oct. 14, 1999.

FIELD OF THE INVENTION

The present invention relates to a novel gene family for "cutaneous T-cell lymphoma associated genes" (CTAGE). The present invention describes two members of this family, CTAGE-1 and CTAGE-2, the underlying cDNA thereof (ctage-1 and ctage-2), and the use thereof for diagnosis and therapy of tumoral diseases.

1. Background of the Invention

The cutaneous T-cell lymphoma (CTCL) is a tumor of the skin which is based on T-lymphocytes and difficult to treat in an advanced stage. The cutaneous T-cell lymphomas are generally counted among the group of non-Hodgkin's lymphomas. The cutaneous T-cell lymphomas comprise inter alia the diseases mycosis fungoides, Sézary syndrome and pagetoid reticulosis. After removing the primary tumor, conventional therapies (irradiation, chemotherapy) often have only little effectiveness in the metastasizing stage of the disease or as a preventive therapy and are also accompanied by the known major side-effects. The tumor has often grown and spread to such an extent that operative treatment is of no use. The measure of a possible immunotherapy (vaccination against tumors) has recently been considered in particular for tumors of the skin. However, the application of such therapy forms requires tumor-specific antigens which have not been found for many tumor types thus far.

2. Description of the Invention

Thus, the invention is substantially based on the problem of discovering tumor-specific antigens which are suited inter alia for cutaneous T-cell lymphomas and can be used for a vaccination therapy.

The solution to this technical problem was obtained by providing the embodiments characterized in the claims.

The inventors were able to isolate a DNA molecule family which in addition to expression in testis tissues is only expressed in different tumor tissues, in particular in the case of T-cell lymphomas (such as the Sézary syndrome), tumors of the HNO region or ovarian cancers (see Examples 4 and 5). They belong to what is called "cancer-testis antigens". The identification of such genes (CTAGE-1 and CTAGE-2) is of interest, since the proteins encoded by them and peptides derived therefrom serve as target structures, e.g. for cytotoxic cells, and can be used as antigens for the production of diagnostic or therapeutic antibodies. For tumor therapy, the peptides encoded by CTAGE-1 or CTAGE-2 or fragments thereof can be either applied directly or loaded on antigen-presenting cells. Peptides presenting the antigens can also be expressed by means of vectors in different cells (e.g. dendritic cells as antigen-presenting cells). Furthermore, cloning of one or more representatives of the CTAGE gene family forms the foundation for developing diagnostic tests to ensure a more reliable and early diagnosis in affected persons in the future. Functional analyses of the protein will no doubt add to the insight into the development of tumors. Thus, they have to be regarded as candidate genes for studying the pathomechanisms on which different tumoral diseases are based.

The present invention therefore relates to a DNA molecule coding for a tumor-associated antigen, comprising:
(a) the nucleic acid of FIG. 1 (SEQ ID NO: 1) or FIG. 2 (SEQ ID NO: 4) or a DNA differing therefrom by one or more base pairs or a fragment thereof,
(b) a DNA hybridizing with the nucleic acid from (a), or
(c) a DNA related to the nucleic acid from (a) or (b) via the degenerated genetic code.

The nucleic acid molecules defined in items (a) and (c) code for proteins, polypeptides or peptides, which still have at least one of the below described biological activities of the protein encoded by the nucleic acid according to FIG. 1 or FIG. 2, e.g. represent a tumor-specific antigen.

The DNA molecules defined in (a) also comprise DNA molecules differing from the sequence indicated in FIGS. 1 and/or 2 by deletion(s), insertion(s), substitution(s) and/or other modifications known in the art, e.g. alternative splicing, or comprise a fragment of the original nucleic acid molecule, the protein encoded by these DNA molecules additionally having one or more of the above described biological activities. Allele variants are also counted thereamong. Methods of producing the above modifications in the nucleic acid sequence are known to a person skilled in the art and are described in standard manuals of molecular biology, e.g. in Sambrook et al., Molecular Cloning: A Laboratory Manual, $2^{nd}$ edition, Cold Spring Harbor Laboratory Press, Cold Spring Harbor N.Y. (1989). In this connection, the variants have a homology of at least 70%, preferably 80%, more preferably 90%, and most preferably 95, 96, 97, 98 or 99%, with the sequences according to FIG. 1 or 2.

The term "hybridizing DNA" refers to a DNA which hybridizes under common conditions, in particular at 20° C. below the melting point of the DNA, with a DNA from (a) In this connection, the term "hybridize" refers to conventional hybridization conditions, preferably to hybridization conditions in which 5×SSPE, 1% SDS, 1× Denhardt's solution is used as the solution and the hybridization temperatures are between 35° C. and 70° C., preferably at 65° C. Following hybridization, it is preferred to first carry out a wash step with 2×SSC, 1% SDS and then with 0.2×SSC at temperatures between 35° C. and 70° C., preferably at 65° C. (for the definitions of SSPE, SSC and Denhardt's solution see Sambrook et al., supra). Stringent hybridization conditions as described in Sambrook et al., supra, for example, are preferred.

In a particularly preferred embodiment the DNA molecule according to the invention is a cDNA.

In another preferred embodiment, the DNA molecule according to the invention is a genomic DNA which is derived preferably from a mammal, e.g. a human being. Screening methods based on nucleic acid hybridization enable the isolation of the genomic DNA molecules according to the invention from any organism or derived genomic DNA libraries, probes being used which contain the nucleic acid sequence indicated in FIG. 1 or 2 or a part thereof.

A nucleic acid according to the invention is particularly suited as an antigen-coding structure for therapeutic purposes. Here, the objective is to stimulate the immune system and/or eliminate tumor cells identified via a member of the CTAGE family, particularly CTAGE-1 or CTAGE-2. There are various possibilities to do so, e.g. giving the patient the naked DNA by way of injection. For this purpose, a plasmid having a very active promoter and a member of the CTAGE family, in particular CTAGE-1 or CTAGE-2, are given by intramuscular or intradermal injection, for example. What is aimed at is that the cells take up the plasmid, produce antigens, present individual peptides via HLA molecules and thus evoke a cytotoxic T-cell immunoresponse which shall then serve for warding off tumor cells. This procedure is described generally in Conry et al., Clinical Cancer Research, Vol. 4, pages 2903-2912 (1998). The gene-gun method is an alternative. It is described in Fynan et al., Proc. Natl. Acad. Sci, U.S.A., Vol. 90, pages 11478-11482 (1993).

The nucleic acids according to the invention can also be inserted in a vector or expression vector. Hence the present invention also comprises vectors containing the nucleic acid molecules. Examples thereof are known to the person skilled in the art. In the case of an expression vector for *E. coli* these are pGEMEX, pUC derivatives (e.g. pUC8), pBR322, pBLueScript, pGEX-2T, pET3b and pQE-8, for example. For expression in yeast e.g. pY100 and Ycpad1 have to be mentioned while e.g. pKCR, pEFBOS, cDM8 and pCEV4 have to be indicated for expression in animal cells. The baculovirus expression vector pAcSGHisNT-A is particularly suited for expression in insect cells. In a preferred embodiment the nucleic acid molecule according to the invention is functionally linked in the vector with regulatory elements which enable the expression thereof in prokaryotic or eukaryotic host cells. Along with the regulatory elements, e.g. a promoter, such vectors contain typically a replication origin and specific genes which enable the phenotypic selection of a transformed host cell. The regulatory elements for expression in prokaryotes, e.g. *E. coli*, comprise the lac-, trp promoter or T7 promoter, and those for expression in eukaryotes comprise the AOX1 or GAL1 promoter in yeast, and those for expression in animal cells include the CMV, SV40, RVS-40 promoter and/or CMV or SV40 enhancer. Further examples of suitable promoters are the metallothionein I and polyhedrin promoters.

Suitable vectors are in particular T7-based expression vectors for expression in bacteria (Rosenberg et al., Gene 56 (1987), 125) or pMSXND for expression in mammalian cells (Lee and Nathans, J. Biol. Chem. 263 (1988), 3521).

The DNA according to the invention can be inserted in a vector not only for the purpose of recombinant production but also to inject using vectors this DNA into patients where it codes for an antigen for therapeutic purposes. In this connection, the DNA is attached in vivo by means of a vector to antigen-presenting cells (APCs), e.g. dendritic cells, for HLA presentation of CTAGE. Here, the vector containing the DNA according to the invention can be injected in different ways:
a) lipid-packed or liposome-packed DNA or RNA, e.g. generally described by Nabel et al., Proc. Natl. Acad. Sci. U.S.A., Vol. 93, pages 15388-15393 (1996);
b) by means of a bacterium as a transport vehicle for the expression vector. Suitable bacteria are e.g. (attenuated) listerias [e.g. *Listeria monocytogenes*], salmonella strains [e.g. *Salmonella* spp.]. This method is described generally by Medina et al., Eur. J. Immunol., 29, pages 693-699 (1999) and Guzman et al., Eur. J. Immunol. 28, pages 1807-1814 (199). Reference is also made to WO 96/14087; Weiskirch et al., Immunological Reviews, Vol. 158, pages 159-169 (1997) and U.S. Pat. No. 5,830,702;
c) by means of gene gun (Williams et al., Proc. Natl. Acad. Sci. U.S.A., Vol. 88, pages 2726-2730, 1991).

In a preferred embodiment, the vector containing the DNA molecules according to the invention is a virus, e.g. an adenovirus, vaccinia virus or an AAV virus, which is of use for a gene therapy. Retroviruses are particularly preferred. Examples of suitable retroviruses are MoMuLV, HaMuSV, MuMTV, RSV or GaLV. The above-mentioned viruses and the fowlpox virus, canarypox virus, influenza virus or sindbis virus are also suited as a basis for a vaccine. Such new vaccines, which after being administered give the patient immunity against tumors, are described in N. Restifo, Current Opinion in Immunology, 8, pages 658-663 1996), or Ying et al., Nature Medicine, Vol. 5, No. 7, page 823 et seq., (1999), for example. For the purpose of gene therapy the DNA molecules according to the invention can also be transported to the target cells in the form of colloidal dispersions. These comprise e.g. liposomes or lipoplexes (Mannino et al., Biotechniques 6 (1988), 682).

General methods known in the art can be used to design vectors or plasmids which contain the DNA molecules according to the invention and suitable control sequences. These methods comprise e.g. in vitro recombination techniques, synthetic methods and in vivo recombination methods, as described in Sambrook et al., supra, for example.

The present invention also relates to host cells containing the above described vectors. These host cells comprise bacteria, yeast, insect and animal cells, preferably mammalian cells. The *E. coli* strains HB101, DH1, x1776, JM101, JM109, BL21, XL1Blue and SG13009, the yeast strain *Saccharomyces cerevisiae* and the animal cells L, 3T3, FM3A, CHO, COS, Vero, HeLa, and the insect cells sf9 are preferred. Methods of transforming these host cells, of phenotypically selecting transformants and expressing the DNA molecules according to the invention using the above described vectors are known in the art.

In order to produce immunity against tumors, it is also preferred to transfect the DNA according to the invention into antigen-presenting cells and give the patient these cells by way of injection. Here, a plasmid is introduced in vitro into an antigen presenting cell (APCs), e.g. dendritic cells, which then produce antigens and present individual peptides via HLA molecules. In this connection, the plasmid DNA can be introduced into the antigen-presenting cells in different ways:
(a) as a naked DNA, e.g. by means of gene gun or electroporation,
(b) lipid-packed or liposome-packed DNA or RNA (Nair et al., Nature Biotechnology, Vol. 16, page 364 et seq. (1998)),
(c) by means of a virus as a vector (Kim et al., J. of Immunotherapy, 20(4), pages 276-286 (1997)),
(d) by means of a bacterium as a transport vehicle for the expression vector (Medina et al., Eur. J. Immunol., 29, pages 693-699 (1999); Guzman et al., Eur. J. Immunol. 28, pages 1807-1814 (1998)).

A clone which codes for a nucleic acid according to the invention (CTAGE-1) was deposited with DSMZ, Deutsche Sammlung von Mikroorganismen und Zellkulturen CmbH [German-type collection of microorganisms and cell cultures], Mascheroder Weg 1b, 38124 Braunschweig, Germany, in accordance with the Budapest Treaty under accession number DSM 13079 (=*Escherichia coli* XL2-Blue pCTAGE-1) on Oct. 7, 1999.

The present invention also relates to a method of producing a protein which is encoded by the above nucleic acids, comprising culturing the above described host cells under conditions enabling the expression of the protein (preferably stable expression) and obtaining the protein from the culture. Suitable methods of recombinantly producing the protein are generally known (see e.g. Holmgren, Annu. Rev. Biochem. 54 (1985), 237; LaVallie et al., Bio/Technology 11 (1993), 187; Wong, Curr. Opin. Biotech. 6 (1995), 517;

Romanos, Curr. Opin. Biotech. 6 (1995), 527; Williams et al., Curr. Opin. Biotech. 6 (1995), 538; and Davies, Curr. Opin Biotech. 6 (1995), 543). Suitable purification methods (e.g. preparative chromatography, affinity chromatography, e.g. immunoaffinity chromatography, HPLC, etc.) are also generally known.

In another embodiment, the present invention relates to a protein encoded by the DNA molecules according to the invention (CTAGE-1 or CTAGE-2) or obtained according to the above method. The protein coding for CTAGE-2 is shown in FIG. 3. In this connection, it is pointed out that the protein according to the invention can be modified according to common methods known in the art. The modifications comprise substitutions, insertions or deletions of amino acids, which modify the structure of the protein, its biological activity being substantially maintained. The substitutions comprise particularly "conservative" substitution of amino acid residues, i.e. substitutions for biologically similar residues, e.g. the substitution of a hydrophobic residue (isoleucine, valine, leucine, methionine, for example) for another hydrophobic residue, or the substitution of a polar residue for another polar residue (e.g. arginine for lysine, glutamic acid for aspartic acid, etc.). Deletions may result in the production of molecules markedly reduced in size, i.e. they lack amino acids at the N-terminus or C-terminus, for example. In this connection, the variants have a homology of at least 70%, preferably 80%, more preferably 90%, most preferably 95, 96, 97, 98 or 99%, with the amino acid sequence derived from the nucleotide sequence according to FIG. 1 or with the amino acid sequence according to FIG. 3.

For the desired anti-tumor vaccination, it is also suited to give the protein or one or more peptides derived therefrom by way of injection. For this purpose, HLA-dependent peptide fragments are determined from the sequence of the protein according to the invention by either corresponding computer programs or experiments (e.g. phagocytotic uptake of the entire protein, then analysis of the presenting peptides). They are produced artificially by methods known to the person skilled in the art and then given to the patient by way of injection (if necessary, with factors stimulating the immune system, e.g. interferons, interleukins etc.). This treatment shall effect that the APCs take up the peptides, present them and thus stimulate in vivo the production of tumor-specific cytotoxic T-cells. This principle is described generally by Melief et al., Current Opinion in Immunology, 8, pages 651-657 (1996).

As described above, the protein according to the invention or fragments thereof can be loaded in vitro on APCs in place of the vector. The loaded cells are then injected into the patient's lymph nodes and provide directly for the stimulation and replication of tumor-specific cytotoxic T-cells (Nestle et al., Nature Medicine, Vol. 4, No. 3, page 328 et seq. (1998); Schadendorf et al., in: Burg, Dummer, Strategies for Immunointerventions in Dermatology, Springer Verlag, Berlin Heidelberg, pages 399-409, 1997). For the purpose of vaccination it may be favorable to modify individual amino acids, as described above, vis-à-vis the wild-type antigen, since under certain circumstances it is in this way possible to increase binding and improve effectiveness (Clay et al., The Journal of Immunology 162: pages 1749-1755, 1999).

The present invention also relates to antibodies which recognize specifically the above described protein CTAGE-1 or CTAGE-2. The antibodies may be monoclonal, polyclonal or synthetic antibodies or fragments thereof, e.g. Fab, Fv or scFv fragments. They are preferably monoclonal antibodies. For the production it is favorable to immunize animals, in particular rabbits or chickens for a polyclonal antibody and mice for a monoclonal antibody, with an above (fusion) protein or with fragments thereof. Further boosters of the animals can be made with the same (fusion) protein or with fragments thereof. The polyclonal antibody can then be obtained from the animal serum or egg yolk. The antibodies according to the invention can be produced according to standard methods, the protein encoded by the DNA molecules according to the invention or a synthetic fragment thereof serving as an immunogen Monoclonal antibodies can be prepared by the method described by Köhler and Milstein (Nature 256 (1975), 495) and Galfré (Meth. Enzymol. 73 (1981), 3), murine myeloma cells being fused with spleen cells originating from immunized mammals. These antibodies can be used e.g. for the immunoprecipitation of the above discussed proteins or for isolating of related proteins from cDNA expression libraries. The antibodies can be bound e.g. in immunoassays in liquid phase or to a solid carrier. Here, the antibodies can be labeled in different ways. Suitable markers and labeling methods are known in the art. Examples of immunoassays are ELISA and RIA. The antibodies can also be used therapeutically along with their diagnostic suitability. In this connection, e.g. a protein of the CTAGE family, e.g. CTAGE-1 or CTAGE-2, serves as a target for bispecific antibodies. Reference is made to Kastenbauer et al. *Laryngorhinootologie,* 78(1), pages 31-35 (1999) and Cao et al., Bioconj. Chem. 9(6), pages 635-644 (1998). As a result of antibody administration, it is possible to counteract the effect of the CTAGE proteins, which supports tumor growth and metastasis.

Furthermore, the use of CTAGE-1 or CTAGE-2 antisense DNA can serve for inhibiting the translation of CTAGE-1 or CTAGE-2 and a therapeutic effect can thus be exerted specifically to this gene. RNA/DNA hybrids form in the corresponding tumor cells, preventing transcription in this way and simultaneously degrading the hybrids (and thus the RNA) by RNaseH (Scanlon et al., The Faseb Journal, Vol. 9, pages 1288-1296, 1995).

The present invention also relates to the use of the above described DNA molecules, vectors, proteins and/or antibodies. They are used preferably for producing a medicament for the diagnosis or treatment of tumoral diseases in which CTAGE-1 or CTAGE-2 plays a role. The provision of a vaccine which as described above is based on either the DNA or the protein/peptide, is preferred.

These medicaments also contain, where appropriate, a pharmaceutically compatible carrier. Suitable carriers and the formulation of such medicaments are known to the person skilled in the art. Suitable carriers comprise e.g. phosphate-buffered common salt solutions, water, emulsions, e.g. oil/water emulsions, wetting agents, sterile solutions, etc. The medicaments can be administered orally or parenterally. The methods of parenteral administration comprise the topical, intra-arterial, intramuscular, subcutaneous, intramedullary, intrathecal, intraventricular, intravenous, intraperitoneal or intranasal administration. The suitable dosage is determined by the attending physician and depends on various factors, e.g. the patient's age, sex and weight, the stage of the disease, the kind of administration, etc.

The present invention also relates to a diagnostic composition which contains the above-described DNA molecule or the antibody or to combinations thereof with a suitable analytical agent, where appropriate. The diagnostic composition is suited on the one hand to detect a tumoral disease but also to carry out a follow-up.

The DNA molecule according to the invention, which is defined as outlined above, can also be used as a probe to isolate DNA molecules which are derived e.g. from another species or another organism and code for a protein having an equal biological activity. For this purpose, the probe has preferably a length of at least 10, more preferably at least 15 bases. Suitable detection methods based on hybridization are known to the person skilled in the art, e.g. Southern or Northern blot. Suitable labeling for the probe is also known to the person skilled in the art and comprises e.g. labeling with radioisotopes, bioluminescence, chemiluminescence, fluorescent markers, metal chelates, enzymes, etc.

In addition, this can also be effected by PCR (Wiedemann et al., PCR Methods Appl. 3, pages 551-564 (1994); Saiki et al., Nature 324, pages 163-166 (1986)) or "ligase chain reaction" (LCR) (Taylor et al., Curr. Opin. Biotechnol. 6, pages 24-29 (1995); Rouwendal et al., Methods Mol. Biol., pages 149-156 (1996)), the primers being derived from the sequence in FIG. 1 or FIG. 2 and the person skilled in the art being able to design suitable primers (as regards length, complementarity with respect to the template, the area to be amplified, etc.) by common methods.

The present invention also relates to a method of diagnosing tumoral diseases in vitro, comprising the steps of:
  isolating nucleic acid from the patient,
  carrying out LCR or PCR with suitable primers or a hybridization analysis with one or more suitable probes based on the coding sequence of FIG. 1 or FIG. 2,
  detecting an amplified product or a hybridization as a reference to the presence of a tumoral disease.

In connection with the above-mentioned method, it is possible to use methods known to the person skilled in the art with respect to the preparation of DNA or RNA from biological samples, the restriction digestion of the DNA, the application of the restriction fragments onto gels separating according to size, e.g. agarose gels, the production and labeling of the probe and the detection of hybridization, e.g. via "Southern blot" or in situ hybridization.

The above detection can also be carried out via PCR or LCR. Here, primers are used, flanking the sequence according to the invention or suitable partial regions. In this connection, amplification products of DNA from the tissue in question, which differ from the amplification products of DNA from healthy tissue as regards the occurrence of CTAGE-1 or CTAGE-2-specific bands, are of diagnostic significance.

In an alternative embodiment, a method can be used which comprises the steps of.
  isolating RNA from the patient,
  carrying out a Northern blot analysis with one or more suitable probes,
  comparing the concentration and/or length of CTAGE-1 or CTAGE-2 mRNA of the patient's sample with an mRNA from a healthy person, the occurrence of CTAGE-1 or CTAGE-2 mRNA referring to a tumoral disease as compared to control mRNA from normal tissue.

In connection with this method, it is possible to use procedures known to the person skilled in the art with respect to the preparation of whole RNA or poly(A)+RNA from biological samples, the application of RNAs onto gels separating according to size, e.g. denaturing agarose gels, the production and labeling of the probe and the detection via "Northern blot".

In another alternative embodiment, a possible disease can also be diagnosed by a method comprising the steps of:
  obtaining a cell sample from a patient,
  contacting the resulting cell sample with the above described antibody according to the invention as a probe under conditions enabling binding of the antibody, binding of the antibody referring to an existing expression of CTAGE-1 or CTAGE-2, which is a reference to a tumoral disease.

This detection can also be carried out using standard techniques known to the person skilled in the art. He is also familiar with cell breaking-up methods which enable the isolation of the protein such that it can be contacted with the antibody. The bound antibody is detected preferably via immunoassays, e.g. Western blot, ELISA, FACS or RIA or immunohistochemical methods. The antibodies are also suited to catch CTAGE-1 or CTAGE-2 overexpressed in tumors so as to inhibit the growth of the tumor, since there is reference to the fact that the occurrence of CTAGE-1 or CTAGE-2 does not only show the presence of tumors but also supports tumor growth actively.

The present invention also relates to kits for carrying out the diagnostic method according to the invention, which contain the antibody according to the invention or a fragment thereof, a DNA molecule according to the invention as a probe or a primer pair suitable for PCR or LCR and based on the sequence of the DNA molecule according to the invention, optionally in combination with a suitable detection means.

Depending on the design of the diagnostic method to be carried out with the kit according to the invention, the DNA molecules, antibodies or fragments thereof, which are contained in the kit, can be immobilized on a suitable carrier.

BRIEF DESCRIPTION OF THE DRAWINGS

The invention is now described in more detail by means of the figures, in which:

FIG. 1 shows a nucleic acid sequence of the cDNA of CTAGE-1 (SEQ ID NO: 1; the complementary nucleotide sequence being set out in the sequence listing hereof as SEQ ID NO: 6), FIG. 2 shows a nucleic acid sequence of the cDNA of CTAGE-2 (SEQ ID NO: 4), FIG. 3 shows an amino acid sequence of CTAGE-2 (SEQ ID NO: 5), FIG. 4 SEREX method.

EXAMPLES

Figure 4:
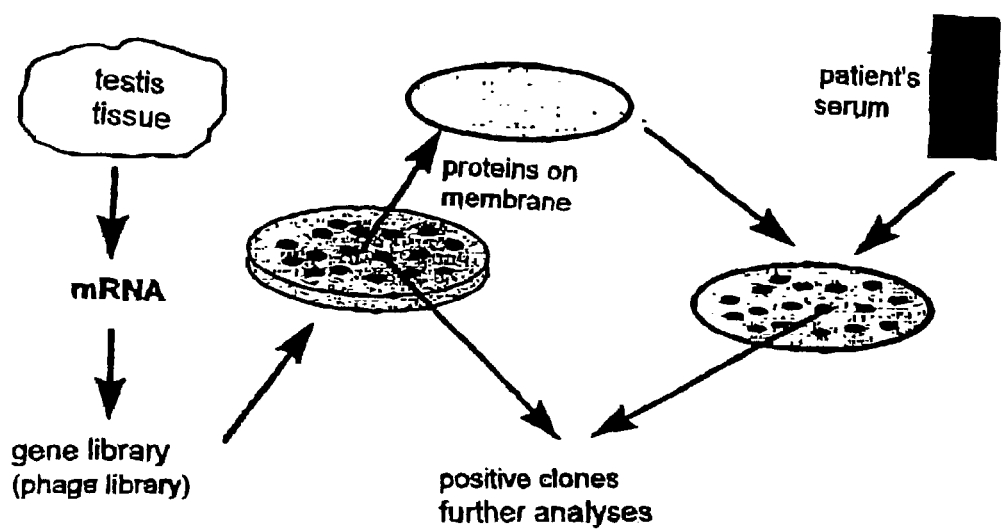

The invention is now described below with reference to the examples.

As regards the methods used reference is made to Sambrook, J., Fritsch, E. F., and Maniatis, T. (Molecular cloning: a laboratory manual; second edition; Cold Spring Harbor Laboratory Press, 1989) and Current Protocols in Molecular Biology (John Wiley and Sons, 1994-1998), the techniques mentioned below, in particular the screening of cDNA libraries, preparation of DNA or RNA, PCR or Northern blot being sufficiently known to, and mastered by, the person skilled in the art.

Example 1

Identification of CTAGE-1 from a cDNA Library Using the SEREX Method

A cDNA phage library (in lambda ZAP) was prepared from mRNA of healthy testis (Uni-ZAP™ XR Custom cDNA Library, Stratagene company, Cat #837201). The library was screened using what is called the SEREX method (Sahin et al., Proc. Natl. Acad. Sci. U.S.A., Vol. 92, pages 11810-11813, 1995). As a result of an analysis of about 1.8×10⁶ recombinant clones of this library with sera from patients suffering from cutaneous T-cell lymphomas (mycosis fungoides, Sézary snydrome), 26 positive clones were obtained. A total of up to 11 sera from diseased patients and 10 sera from control persons were used in the serological analysis of the clones found. It is interesting that none of the clones was detected by control sera (from healthy persons) but by several sera from diseased patients. The clones were sequenced, and the sequence shown in FIG. 1 was determined for one of the clones. It was named CTAGE-1.

The procedure according to the invention is shown in enclosed FIG. 4.

In the SEREX variant chosen, mRNA from healthy testis is isolated and a cDNA phage library is prepared therefrom. The library is transduced into *E. coli* and the expressed proteins are blotted onto nitrocellulose membranes. Thereafter, preabsorbed patient's serum is used to screen for reactive clones. Positive clones are isolated from the agar and sequenced.

Example 2

Preparation and Purification of a CTAGE-1 Protein According to the Invention

In order to produce a CTAGE-1 protein according to the invention, the DNA of FIG. 1 is provided with BamHI linkers, subsequently cut using BamHI and inserted in the expression vector pQE-8 cleaved by BamHI (Qiagen company). The expression plasmid pQ/CTAGE-1 is obtained. It codes for a fusion protein comprising 6 histidine residues (N-terminus partner) and the CTAGE-1 protein according to the invention (C-terminus partner). pQ/CTAGE-1 is used to transform *E. coli* SG13009 (cf. Gottesmann, S. et al., J. Bacteriol. 148, (1981), 265-273). The bacteria are cultured in an LB broth with 10 µg/ml ampicillin and 25 µg/ml kanamycin and induced with 60 µM isopropyl-β-D-thiogalactopyranoside (IPTG) for 4 h. Lysis of the bacteria is achieved by the addition of 6 M guanidine hydrochloride. Thereafter, the lysate is chromatographed (Ni-NTA resin) in the presence of 8 M urea in accordance with the manufacturer's instructions (Qiagen company). The bound fusion protein is eluted in a buffer having a pH of 3.5. After its neutralization, the fusion protein is subjected to 18% SDS polyacrylamide gel electrophoresis and stained with coomassie blue (cf. Thomas, J. O. and Kornberg, R. D., J. Mol. Biol. 149 (1975), 709-733).

It shows that a (fusion) protein according to the invention can be prepared in highly pure form.

Example 3

Preparation and Detection of an Antibody According to the Invention

A fusion protein of Example 2 according to the invention is subjected to 18% SDS polyacrylamide gel electrophoresis. After staining the gel with 4 M sodium acetate, the corresponding band is cut out of the gel and incubated in phosphate-buffered common salt solution. Gel pieces are sedimented before the protein concentration of the supernatant is determined by SDS polyacrylamide gel electrophoresis which is followed by coomassie blue staining. Animals are immunized as follows with the gel-purified fusion protein:

Immunization Protocol for Polyclonal Antibodies in Rabbits

35 µg of gel-purified fusion protein in 0.7 ml PBS and 0.7 ml complete or incomplete Freund's adjuvant are used per immunization:

| Day 0:  | 1st immunization (complete Freund's adjuvant) |
|---------|-----------------------------------------------|
| Day 14: | 2nd immunization (incomplete Freund's adjuvant; icFA) |
| Day 28: | 3rd immunization (icFA) |
| Day 56: | 4th immunization (icFA) |
| Day 80: | bleeding to death. |

The rabbit serum is tested in an immunoblot. For this purpose, a fusion protein of Example 2 according to the invention is subjected to SDS polyacrylamide gel electrophoresis and transferred to a nitrocellulose filter (cf. Khyse-Andersen, J., J. Biochem. Biophys. Meth. 10 (1984), 203-209). The Western blot analysis is carried out as described in Bock, C.-T. et al., Virus Genes 8, (1994), 215-229. For this purpose, the nitrocellulose filter is incubated with a first antibody at 37° C. for one hour. This antibody is the rabbit serum (1:10,000 in PBS). After several wash steps using PBS, the nitrocellulose filter is incubated with a second antibody. This antibody is an alkaline phosphatase-coupled monoclonal goat anti-rabbit IgG antibody (Dianova company) (1:5,000) in PBS. 30 minutes of incubation at 37° C. are followed by several wash steps using PBS and subsequently by the alkaline phosphatase detection reaction with developer solution (36 µM 5'-bromo-4-chloro-3-indolylphosphate, 400 µM nitro blue tetrazolium, 100 mM Tris-HCl, pH 9.5, 100 mM NaCl, 5 mM $MgCl_2$) at room temperature until bands become visible.

It turns out that polyclonal antibodies according to the invention can be prepared.

Immunization Protocol for Polyclonal Antibodies in Chickens

40 µg of gel-purified fusion protein in 0.8 ml PBS and 0.8 ml complete or incomplete Freund's adjuvant are used per immunization.

| Day 0:  | 1st immunization (complete Freund's adjuvant) |
|---------|-----------------------------------------------|
| Day 28: | 2nd immunization (incomplete Freund's adjuvant; icFA) |
| Day 50: | 3rd immunization (icFA) |

Antibodies are extracted from egg yolk and tested in a Western blot. Polyclonal antibodies according to the invention are detected.

Immunization Protocol for Monoclonal Antibodies in Mice

12 µg of gel-purified fusion protein in 0.25 ml PBS and 0.25 ml complete or incomplete Freund's adjuvant are used per immunization. The fusion protein is dissolved in 0.5 ml (without adjuvant) in the 4$^{th}$ immunization.

| Day 0:  | 1st immunization (complete Freund's adjuvant) |
|---------|-----------------------------------------------|
| Day 28: | 2nd immunization (incomplete Freund's adjuvant; icFA) |
| Day 56: | 3rd immunization (icFA) |
| Day 84: | 4th immunization (PBS) |
| Day 87: | fusion. |

Supernatants of hybridomas are tested in a Western blot. Monoclonal antibodies according to the invention are identified.

Example 4

Northern Blots

Northern blots with mRNAs from different healthy tissues were hybridized at 50° C. overnight in a hybridization buffer with 2×SSC, tenfold Denhardt's solution, 10% dextransulfate, 1% SDS, 3% SSC and 0.1 mg/ml salmon sperm DNA and the specific probe. The specific probe was prepared by radioactive labeling (random-primed DNA-labeling kit; Roche-Diagnostics) of the PCR product from a PCR carried out on testis control cDNA as described below in Example 5. The filters were washed once each at 65° C. in 2×SSC/0.1% SDS and in 0.2×SSC/0.1% SDS and a Kodak film or Fuji film 24 was exposed therewith at −70° C. for up to 7 days.

The Northern blot showed that CTAGE-1 can only be detected in testis but not in control tissue.

Example 5

Diagnosis of Tumors by Means of PCR mRNA was obtained from different tissues and blood using the "RNAclean" kit (AGS-Hybaid company, Heidelberg, Germany) in accordance with the manufacturer's instructions. The RNA was treated with DNAse, and a cDNA was prepared by means of the cDNA kit from Roche Diagnostics. For this purpose, 1 µg RNA and 20 U AMV reverse transcriptase are used by adding 1.6 µg RNAse inhibitor in a total volume of 20 µl. The procedure was carried out according to the manufacturer's instructions. The cDNA obtained from the RNA was checked for the presence of CTAGE-1 by means of polymerase chain reaction using CTAGE-1-specific primers. The PCR conditions were as follows:

5 µl (about 100 ng) cDNA to be amplified
    16 mM $(NH_4)_2SO_4$
    67 mM Tris-HCl, pH 8.8
    1.5 mM $MgCl_2$
    0.01% Tween 20
    200 µM dGTP
    200 µM dCTP
    200 µM dTTP
    200 µM dATP
    1 U Taq-DNA polymerase per batch (=25 µl)
    400 nM primer 1
    400 nM primer 2
    10% DMSO
    95° C., 5 min.
    for 35 cycles: 95° C. for 1 min., 60° C. for 1 min., 72° C. for 2 min.,
    72° C. for 10 min.

primer 1: 5'-CTC CTG ACT TCT TTC CCA ACC TTT ACC-3' (SEQ ID NO: 2)

primer 2: 5'-TGC AAT TCC CAC CTA ACT TCC ATT CTG-3' (SEQ ID NO: 3)

Following the electrophoretic separation on an agarose gel (1.5%) the amplificates were made visible by ethidium bromide.

The results are as follows:

Control Tissue:

When cDNA from testis tissue was used, the PCR was positive using the indicated primers whereas all the tissues given below showed a negative result:

intestines, small intestine, fetal liver, fetal lungs, fetal spleen, fetal kidney, fetal skeletal muscle, fetal thymus, fetal brain, fetal heart, brain, skin, heart, bone, liver, lungs, stomach, spleen, kidney, ovary, pancreas, peripheral blood lymphocytes, placenta, prostate, skeletal muscle, T-lymphocytes (activated), thymus, trachea tumoral tissue (cutaneous T-cell lymphoma; 6 of 17 positive=35%);

| | |
|---|---|
| *mycosis fungoides*: | 4 of 13 positive |
| T-zone lymphoma: | 1 of 1 positive |
| Sézary syndrome: | 1 of 2 positive |
| CD30 lymphoma: | 0 of 1 positive |

Tumor tissue of ovarian tumors (19 of 59 positive=32%);

| | |
|---|---|
| Tumor | 17 of 59 positive |
| Relapse | 2 of 4 positive |

Tumor tissue of tumors from the HNO site (5 of 27 positive<19%);

| | |
|---|---|
| Auditory canal | 0 of 1 positive |
| Hypopharynx | 1 of 3 positive |
| Carcinosarcoma parotic | 0 of 1 positive |
| Larynx | 2 of 12 positive |
| Nasal pharynx | 0 of 1 positive |
| Orbita | 0 of 1 positive |
| Oropharynx | 2 of 8 positive |
| Cell lines: | |
| Lymphoma cell lines: | 4 of 4 positive (100%) |
| Leukemia cell lines: | 0 of 6 positive (0%) |
| Melanoma cell lines: | 0 of 20 positive (0%) |

Example 6

Identification of CTAGE-2

CTAGE-2 was identified by means of Race PCR (Clontech company, Heidelberg).

1. Kits/Reagents

SMART™ cDNA amplification kit.

Advantage® 2 polymerase PCR kit

MMLV reverse transcriptase (Gibco company, Cat. #18064-014)

2. Preparation of SMART™ cDNA

5' 1 RACE Ready cDNA
    1 µg RNA (testis)
    1 µl 5' CDS primer
    1 µl SMART II oligo 3' RACE Ready cDNA
    1 µg RNA (testis)
    1 µl 3' CDS primer fill up with H₂O to a volume of 5 µl each incubate 2 min. at 72° C.

ice for 2 min.

centrifuge

2 µl 5× first strand buffer

1 µl DTT (20 mM)

1 µl dNTP Mix (10 mM)

1 µl MMLV reverse transcriptase (200 U/µl)

mix by pipetting centrifuge incubate at 42° C. for 1.5 h stop the reaction with Tricina EDTA buffer:

20 µl with RNA <200 ng

100 µl with RNA >200 ng

250 µl with mRNA incubate at 72° C. for 7 min.

store at −20° C.

3. Primer Selection

The primers should have a length of about 23-28 nucleotides and a very high annealing temperature (most suitably above 70° C.). The primer extended in the 5' direction should be located near the 5' end and the 3'-extending one should be located near the 3' end. A person skilled in the art knows how to select the primers.

The 5'-extending primer is a reverse primer and referred to as Race 1, the 3'-extending primer is a forward primer and is referred to as Race 2.

4. Race PCR

4.1 Preparation prepare master mix

| PCR Grade Water | 34.5 µl | 17.25 µl |
| --- | --- | --- |
| 10× Advantage 2 buffer | 5 µl | 2.5 µl |
| DNTP mix | 1 µl | 0.5 µl |
| 50× Advantage 2 poly | 1 µl | 0.5 µl |

Control PCR 1:

| 5' cDNA | 1.25 µl | 3' Race cDNA | 1.25 µl |
| --- | --- | --- | --- |
| UPM 10× | 2.5 µl | UPM 10× | 2.5 µl |
| 5' Race TFR primer | 0.5 µl | 3' Race TFR primer | 0.5 µl |
| H₂O | — | H₂O | — |
| Master mix | 20.75 µl | Master mix | 20.75 µl |

Touch Down PCR

94° C., 5 min.

94° C., 0.3 min. 5×; 94° C., 0.3 min. 5×; 94° C., 0.3 min. 25×

70° C., 0.3 min. 5×; 68° C., 0.3 min. 5×; 66° C., 0.3 min. 25×

72° C., 3 min. 5×; 72° C., 3 min. 5×; 72° C., 3 min. 25×

72° C., 10 min.

4° C., storing

Expected Result:

5': 2.6 kb

3': 2.9 kb (sometimes 0.6 kb)

result: cDNA o.k.

4.2 Carrying Out Race PCR pipetting scheme

5' direction:

| | Race | Negative control | Negative control |
| --- | --- | --- | --- |
| 5' cDNA | 2.5 µl | 1.25 µl | 1.25 µl |
| UPM 10× | 5 µl | 2.5 µl | 2.5 µl |
| Race 1 primer | 1 µl | — | 0.5 µl |
| Control primer: TFR 5' | — | 0.5 | — |
| H₂O | — | — | — |
| Master mix | 41.5 µl | 20.75 µl | 20.75 µl |

3' direction;

| | Race | Negative control | Negative control |
| --- | --- | --- | --- |
| 3' cDNA | 2.5 µl | 1.25 µl | 1.25 µl |
| UPM 10× | 5 µl | — | 2.5 µl |
| Race 1 primer | 1 µl | — | — |
| Control primer: TFR 5' | — | 0.5 µl | — |
| H₂O | — | 2.5 µl | 0.5 µl |
| Master mix | 41.5 µl | 20.75 µl | 20.75 µl |

Program: Touch Down PCR

94° C., 5 min.

94° C., 0.3 min. 5×; 94° C., 0.3 min. 5×; 94° C., 0.3 min. 25×

70° C., 0.3 min. 5×; 68° C., 0.3 min. 5×; 66° C., 0.3 min. 25×

72° C., 3 min. 5×; 72° C., 3 min. 5×; 72° C., 3 min. 25×

72° C., 10 min.

4° C., storing

Result

Negative controls: no amplification

Race: amplification has taken place

Alternatives when Race only supplies "smear": nested Race

For this purpose, dilute PCR amplificate of 1$^{st}$ Race 1:50 in Tris EDTA buffer Nested Race:

Modified pipetting scheme: in place of 5 µl UPM, 1 µl NUP (nested Universal Primer Mix)

in place of Race 1, nested Race β

Modified PCR program: in place of Touch Down PCR, 15 cycles nes-Race

94° C., 5 min.

94° C., 0.3 min. 15×

68° C., 0.3 min. 15×

72° C., 3 min. 15×

72° C., 10 min.

4° C., storing

The cDNA ends are rapidly amplified by the described procedure:

5.1 cDNA Synthesis 5.1.1. 3'

3'cDNA synthesis uses a normal reverse transcriptase reaction with an initial oligo dT primer hybridized at the Poly A end.

The 3'CDS (dT OligoMix) mix also contains the Smart OligoII (in minor concentration) (see 5.2.2) so that 5' full length polymerization takes place. A known sequence is attached to the Oligo dT primer (=Smart).

5.1.2 5'

Like 3' synthesis, 5'cDNA synthesis is started by Oligo dT (5'CDS Mix) at the 3' end of the mRNA.

The SmartII Oligo system makes use of the special fact that following full-length transcription reverse transcriptase MMLV adopts terminal transferase activity which attaches 3-5 nucleotides (predominantly dCtp) to the newly synthesized strand ($1^{st}$ strand).

The SMART II Oligo can bind to this site rich in cytosine, since it has a site rich in guanine. A known sequence (Smart II Oligo) is attached thereto. The SMART II Oligo now serves as a primer for reverse transcription in the 3' direction. The MMLV transcriptase only attaches a site rich in cytosine to fully polymerized mRNAs so as to ensure that only full length cDNAs form.

5.2 Race PCR:

5.2.1 Advantage 2 Polymerase Mix

Advantage Taq™ polymerase

Proof reading polymerase

Taq Start™ antibody

Proof reading effects perfect polymerization.

The antibody effects an automatic hot start PCR. The monoclonal antibody binds to the N-terminus of Taq polymerase, thus inhibiting its activity. In the initial heating step to 95° C., the antibody is denatured, and the polymerase is no longer inhibited.

All in all, this combination enables a polymerase reaction over long distances.

5.2.2 PCR

Race PCR utilizes the fact that the SMART full-length cDNA is limited by known sequences. They serve as forward/reverse primers for amplification.

The known sequence attached to Oligo dT at the 3'CDS primer mix, is the same as that represented by the SMART Oligo II attachment to the sequence in guanine.

The invention claimed is:

1. An isolated nucleic acid which codes for a protein of the CTAGE family and has expression in malignant tumors and in ordinary testis tissue, wherein the nucleic acid consists of the nucleic acid of SEQ ID NO: 1.

2. The nucleic acid according to claim 1, which consists of cDNA.

3. A vector comprising the nucleic acid according to claim 1.

4. The vector according to claim 3, wherein the nucleic acid is functionally linked with regulatory elements which enable the expression in prokaryotic or eukaryotic host cells.

5. The vector according to claim 4, which is selected from the group consisting of: plasmid, bacterium, virus and retrovirus.

6. An isolated transformant, containing the vector according to claim 5.

7. The isolated transformant according to claim 6, which is selected from the group consisting of: bacterium, a yeast cell, insect cell, animal and mammalian cell.

8. A method of preparing an antigen-protein encoded by the nucleic acid according to claim 1, comprising culturing an isolated transformant comprising a vector containing SEQ ID NO:1 under conditions enabling the expression of the protein and collecting the protein from the culture.

* * * * *